United States Patent
Smith

(10) Patent No.: US 9,028,521 B2
(45) Date of Patent: May 12, 2015

(54) OBTURATOR TIPS

(75) Inventor: Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 866 days.

(21) Appl. No.: 12/128,752

(22) Filed: May 29, 2008

(65) Prior Publication Data

US 2008/0300617 A1  Dec. 4, 2008

Related U.S. Application Data

(60) Provisional application No. 60/932,811, filed on Jun. 1, 2007.

(51) Int. Cl.
*A61B 17/00* (2006.01)
*A61B 17/34* (2006.01)

(52) U.S. Cl.
CPC ..... *A61B 17/3417* (2013.01); *A61B 2017/3456* (2013.01); *A61B 2017/346* (2013.01)

(58) Field of Classification Search
CPC ................... A61B 17/3417; A61B 2017/3454; A61B 2017/3456; A61B 2017/3458; A61B 2017/346
USPC .......... 606/185, 190, 191, 167, 184; 604/104, 604/164.11, 164.01–164.13, 264
See application file for complete search history.

(56) References Cited

U.S. PATENT DOCUMENTS

| 2,566,738 | A | | 9/1951 | Mitchell |
|---|---|---|---|---|
| 3,760,810 | A | | 9/1973 | Van Hoorn |
| 4,654,030 | A | | 3/1987 | Moll et al. |
| 4,878,485 | A | | 11/1989 | Adair |
| 5,057,082 | A | * | 10/1991 | Burchette, Jr. ........... 604/164.06 |
| 5,169,397 | A | | 12/1992 | Sakashita et al. |
| 5,224,951 | A | | 7/1993 | Freitas |
| 5,224,952 | A | | 7/1993 | Deniega et al. |
| 5,226,890 | A | | 7/1993 | Ianniurberto et al. |
| 5,250,068 | A | | 10/1993 | Ideguchi et al. |
| 5,256,149 | A | | 10/1993 | Banik et al. |
| 5,263,937 | A | | 11/1993 | Shipp |
| 5,271,380 | A | | 12/1993 | Riek et al. |
| 5,290,276 | A | | 3/1994 | Sewell, Jr. |
| 5,334,150 | A | | 8/1994 | Kaali |
| 5,354,302 | A | | 10/1994 | Ko |

(Continued)

FOREIGN PATENT DOCUMENTS

EP  1 685 792 A  8/2006
EP  1685792 A  8/2006

(Continued)

OTHER PUBLICATIONS

European Search Report for corresponding EP 08251871 date of mailing is Sep. 29, 2008 (3 pages).

(Continued)

*Primary Examiner* — Katherine Dowe

(57) ABSTRACT

A surgical instrument for use with a surgical portal apparatus is disclosed. The surgical instrument includes an elongate shaft and a dilating member disposed at the distal end of the elongate shaft. The elongate shaft has proximal and distal ends and defines a longitudinal axis. The dilating member has an outer surface that includes at least one atraumatic edge member. The at least one atraumatic edge member extends proximally from a tip of the dilating member. The dilating member has a first substantially triangular cross-section disposed transverse to the longitudinal axis.

15 Claims, 11 Drawing Sheets

(56) References Cited

U.S. PATENT DOCUMENTS

| | | |
|---|---|---|
| 5,370,640 A | 12/1994 | Kolff |
| 5,372,588 A | 12/1994 | Farley et al. |
| 5,376,076 A | 12/1994 | Kaali |
| 5,380,291 A | 1/1995 | Kaali |
| 5,385,572 A | 1/1995 | Nobles et al. |
| 5,408,992 A | 4/1995 | Hamlin et al. |
| 5,431,151 A | 7/1995 | Riek et al. |
| 5,441,041 A | 8/1995 | Sauer et al. |
| 5,445,142 A | 8/1995 | Hassler, Jr. |
| 5,467,762 A | 11/1995 | Sauer et al. |
| 5,478,327 A * | 12/1995 | McGregor et al. ............ 604/272 |
| 5,534,009 A | 7/1996 | Lander |
| 5,551,947 A | 9/1996 | Kaali |
| 5,562,696 A | 10/1996 | Nobles et al. |
| 5,569,160 A | 10/1996 | Sauer et al. |
| 5,569,291 A | 10/1996 | Privitera et al. |
| 5,569,292 A | 10/1996 | Scwemberger et al. |
| 5,571,133 A | 11/1996 | Yoon |
| 5,591,191 A | 1/1997 | Kieturakis |
| 5,591,192 A | 1/1997 | Privitera et al. |
| 5,609,562 A | 3/1997 | Kaali |
| 5,632,717 A | 5/1997 | Yoon |
| 5,645,076 A | 7/1997 | Yoon |
| 5,658,236 A | 8/1997 | Sauer et al. |
| 5,658,306 A | 8/1997 | Kieturakis et al. |
| 5,662,613 A | 9/1997 | Astarita |
| 5,662,673 A | 9/1997 | Kieturakis |
| 5,674,184 A | 10/1997 | Hassler, Jr. |
| 5,676,682 A | 10/1997 | Yoon |
| 5,681,323 A | 10/1997 | Arick |
| 5,685,820 A | 11/1997 | Riek et al. |
| 5,690,663 A | 11/1997 | Stephens |
| 5,707,382 A | 1/1998 | Sierocuk et al. |
| 5,720,761 A | 2/1998 | Kaali |
| 5,730,755 A * | 3/1998 | Yoon ........................... 606/185 |
| 5,738,628 A | 4/1998 | Sierocuk et al. |
| 5,772,678 A | 6/1998 | Thomason et al. |
| 5,797,944 A | 8/1998 | Nobles et al. |
| 5,807,317 A | 9/1998 | Krech, Jr. |
| 5,807,338 A | 9/1998 | Smith et al. |
| 5,817,061 A | 10/1998 | Goodwin et al. |
| 5,843,039 A | 12/1998 | Klemm |
| 5,843,115 A | 12/1998 | Morejon |
| 5,857,999 A | 1/1999 | Quick et al. |
| 5,860,996 A | 1/1999 | Urban et al. |
| 5,873,889 A | 2/1999 | Chin |
| 5,916,232 A | 6/1999 | Hart |
| 5,980,549 A | 11/1999 | Chin |
| RE36,434 E | 12/1999 | Hamlin |
| 6,007,481 A | 12/1999 | Riek et al. |
| 6,099,544 A | 8/2000 | Wolf et al. |
| 6,106,539 A | 8/2000 | Fortier |
| 6,168,607 B1 | 1/2001 | Wattiez et al. |
| 6,176,824 B1 | 1/2001 | Davis |
| 6,203,557 B1 | 3/2001 | Chin |
| 6,206,823 B1 | 3/2001 | Kolata et al. |
| 6,228,059 B1 | 5/2001 | Astarita |
| 6,238,407 B1 | 5/2001 | Wolf et al. |
| D443,360 S | 6/2001 | Haberland |
| D449,887 S | 10/2001 | Haberland et al. |
| 6,306,053 B1 * | 10/2001 | Liechty, II .................... 473/583 |
| 6,478,806 B2 | 11/2002 | McFarlane |
| 6,544,277 B1 | 4/2003 | O'Heeron et al. |
| 6,685,630 B2 | 2/2004 | Sauer et al. |
| 6,692,467 B2 | 2/2004 | McFarlane |
| 6,695,816 B2 | 2/2004 | Cassidy, Jr. |
| 6,830,578 B2 | 12/2004 | O'Heeron et al. |
| 6,835,201 B2 | 12/2004 | O'Heeron |
| 6,884,253 B1 | 4/2005 | McFarlane |
| 6,960,164 B2 | 11/2005 | O'Heeron |
| 6,989,003 B2 | 1/2006 | Wing et al. |
| 2001/0029388 A1 | 10/2001 | Kieturakis et al. |
| 2002/0099289 A1 | 7/2002 | Crowley |
| 2002/0115918 A1 | 8/2002 | Crowley |
| 2002/0133188 A1 | 9/2002 | O'Heeron |
| 2002/0143236 A1 | 10/2002 | Sauer et al. |
| 2002/0188201 A1 | 12/2002 | Crowley |
| 2003/0100914 A1 | 5/2003 | O'Heeron et al. |
| 2003/0187471 A1 | 10/2003 | Cooper |
| 2004/0015182 A1 | 1/2004 | Kieturakis et al. |
| 2004/0230217 A1 | 11/2004 | O'Heeron |
| 2005/0033304 A1 | 2/2005 | O'Heeron |
| 2005/0038466 A1 | 2/2005 | O'Heeron et al. |
| 2005/0107816 A1 * | 5/2005 | Pingleton et al. .............. 606/185 |
| 2005/0203559 A1 | 9/2005 | O'Heeron |
| 2005/0251190 A1 | 11/2005 | McFarlane |
| 2006/0264905 A1 * | 11/2006 | Eskridge et al. .............. 604/523 |

FOREIGN PATENT DOCUMENTS

| | | |
|---|---|---|
| JP | 2002-028165 | 1/2002 |
| WO | WO 2008/045316 A | 4/2008 |
| WO | WO2008/045316 A | 4/2008 |

OTHER PUBLICATIONS

European Search Report for corresponding EP06001607 dated Mar. 13, 2006.

English translation of Japanese Office Action from Japanese Application No. 2008-142983 mailed Oct. 12, 2012.

European Search Report from EP Application No. EP 10 25 2127 mailed Apr. 17, 2012.

European Search Report from EP Application No. EP 11 00 4282 mailed Feb. 10, 2014, 5 pages.

* cited by examiner

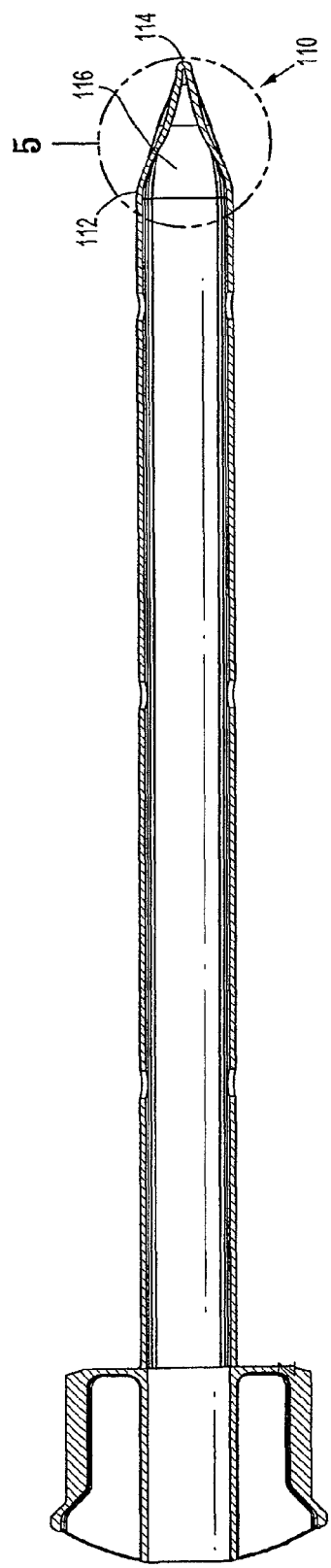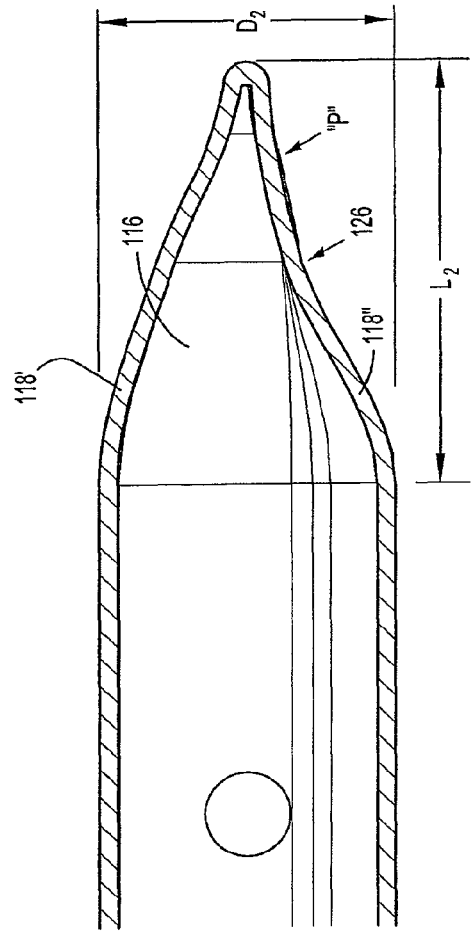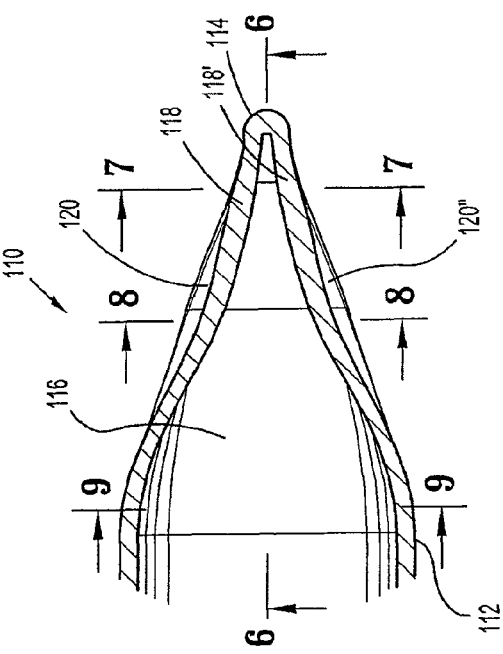
FIG. 4
FIG. 6
FIG. 5

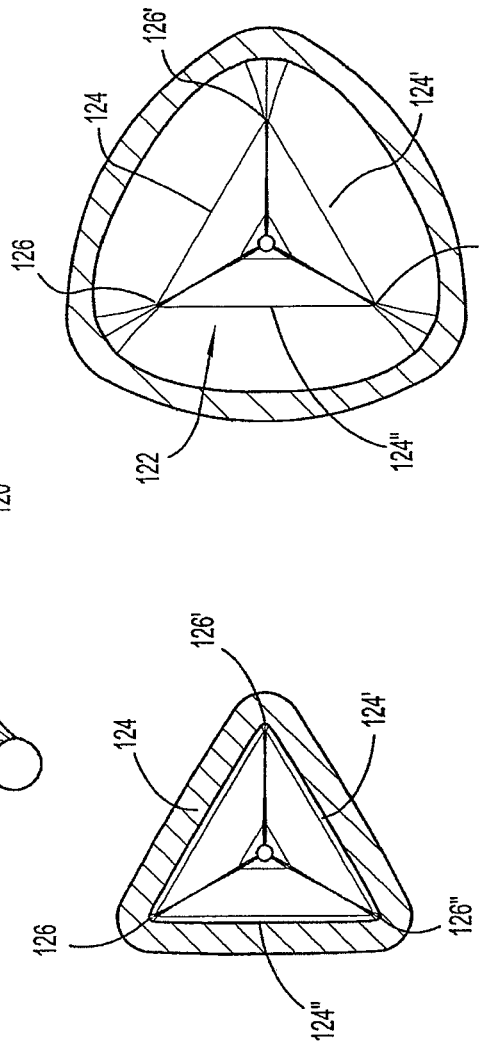
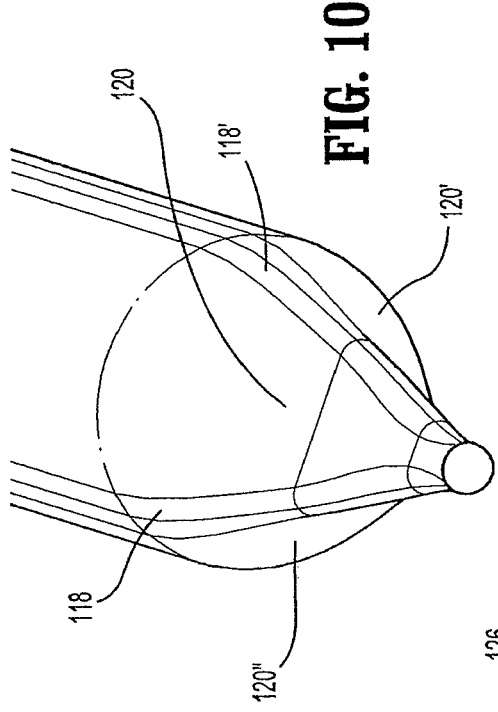
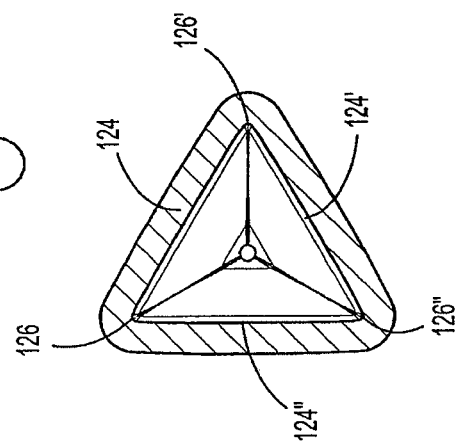
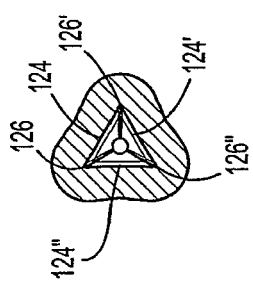

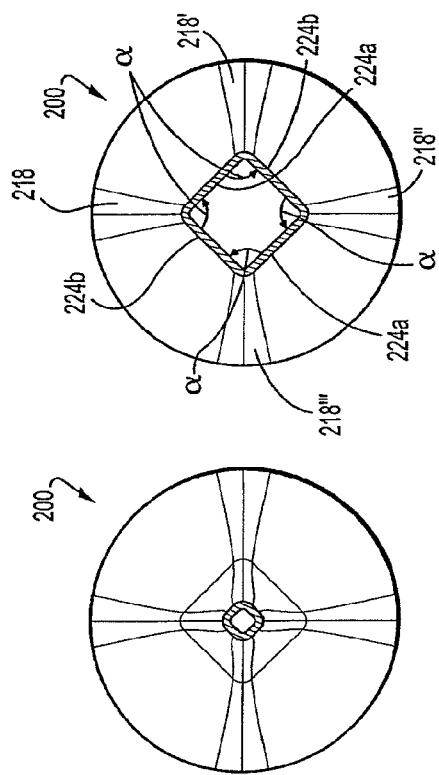
FIG. 15
FIG. 14
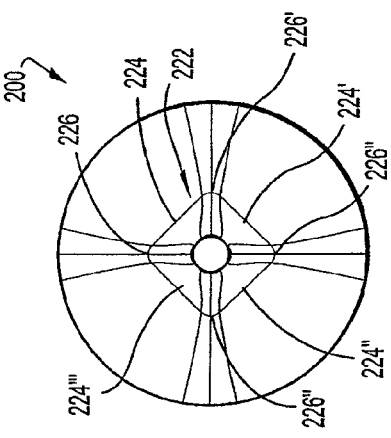
FIG. 17
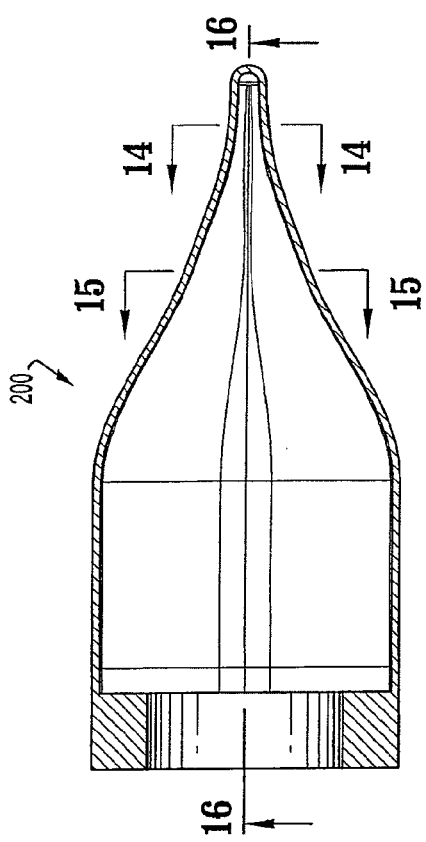
FIG. 13
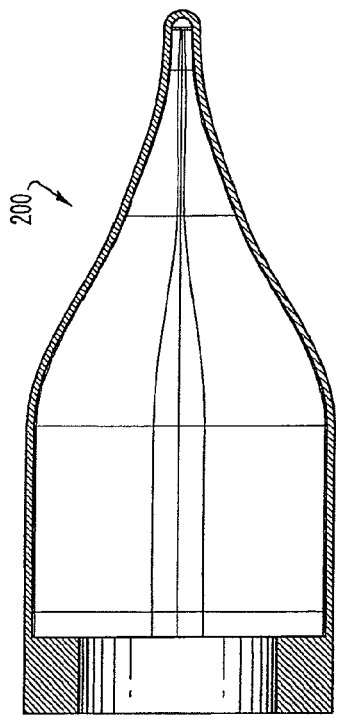
FIG. 16

OBTURATOR TIPS

CROSS REFERENCE TO RELATED APPLICATION

The present application claims the benefit of and priority to U.S. Provisional Application Ser. No. 60/932,811 filed on Jun. 1, 2007, the entire contents of which are incorporated herein by reference.

BACKGROUND

1. Technical Field

The present disclosure is directed towards an instrument for use in surgical procedures. More particularly, the present disclosure relates to an obturator or dilating device that includes an inventive dilating tip for use with a surgical portal or access assembly, such as a trocar or cannula assembly, during endoscopic and laparoscopic procedures.

2. Background of Related Art

Generally, endoscopic and laparoscopic surgical procedures are performed through surgical access devices that include narrow tubular sleeves or cannulas in an insufflated workspace inserted percutaneously into a patient through a small incision, puncture, or access point.

Initially, the incision or access point created is the tissue is very small so as to minimize both tissue trauma and the invasive nature of the procedure. However, to facilitate the insertion of the access device into the patient's tissue, it is often necessary to enlarge or dilate the access point using a surgical instrument such as an obturator, stylet, or trocar. Given the design of known surgical instrument tips, substantial force may be required to force the instrument through the access point and thereby dilate the opening, potentially resulting in damage or trauma to the tissue surrounding the access point as well as the internal surgical site. Accordingly, there exists a need in the art for a surgical instrument that includes an improved tip which facilitates the dilation of a percutaneous access point and curtails the risk of tissue damage.

SUMMARY

The present disclosure relates to improvements in accessing body tissue during endoscopic procedures, laparoscopic procedures, and the like. In one embodiment, a surgical instrument for use with a surgical portal apparatus is disclosed that includes a dilating member disposed at a distal end of an elongate shaft that defines a longitudinal axis. The dilating member has an outer surface that includes at least one atraumatic edge member extending outwardly therefrom and proximally from a distal, substantially tip. In one embodiment, that at least one edge member extends at least partially along the elongate shaft of the instrument. In another embodiment, the dilating member has a substantially tapered profile.

The dilating member has a substantially polygonal cross-section that may be substantially triangular in one embodiment. In additional embodiments, the substantially polygonal cross-section includes at least two sides that are in substantially parallel relation, which may include a first set of sides and at least one additional set of sides, e.g. a second set of sides that define a plurality of vertices. The plurality of vertices may be either substantially angular or substantially rounded in configuration and may include at least one vertex that is less than or equal to 90°.

The elongate shaft of the instrument defines a centerpoint that is either substantially aligned with, or substantially offset from, the tip of the dilating member.

BRIEF DESCRIPTION OF THE DRAWINGS

The accompanying drawings, which are incorporated in, and constitute a part of this specification, illustrate embodiments of the disclosure and, together with a general description of the disclosure given above and the detailed description of the embodiment(s) given below, serve to explain the principles of the disclosure, wherein:

FIG. 4 is a side cross-sectional view of the dilating instrument of FIG. 1;

FIG. 5 is a side cross-sectional view of a dilating member disposed at a distal end of the dilating instrument of FIG. 1;

FIG. 6 is a longitudinal cross-sectional view of the dilating member taken along lines 6-6 of FIG. 5;

FIG. 7 is a front cross-sectional view of the dilating member taken along lines 7-7 of FIG. 5;

FIG. 8 is a front cross-sectional view of the dilating member taken along lines 8-8 of FIG. 5;

FIG. 9 is a front cross-sectional view of the dilating member taken along lines 9-9 of FIG. 5;

FIG. 10 is a front perspective view of the dilating member;

FIG. 13 is a side cross-sectional view of the dilating member of FIG. 11;

FIG. 14 is a front view of the dilating member taken along lines 14-14 of FIG. 13;

FIG. 15 is a front view of the dilating member taken along lines 15-15 of FIG. 13;

FIG. 16 is a longitudinal cross-sectional view of the dilating member taken along lines 16-16 of FIG. 13;

FIG. 17 is a front view of the dilating member of FIG. 11;

DESCRIPTION OF EMBODIMENTS

Figure 1:
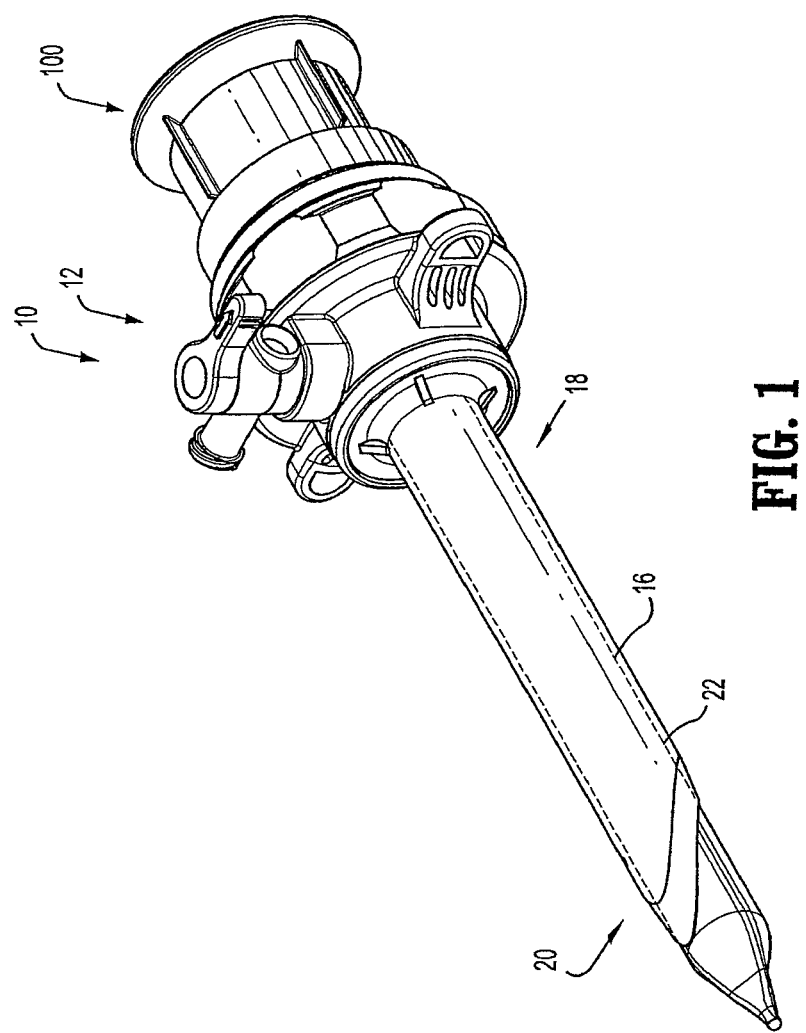
FIG. 1 is a side perspective view of a surgical portal system in conjunction with a dilating instrument in accordance with the principles of the present disclosure.
Figure 3:
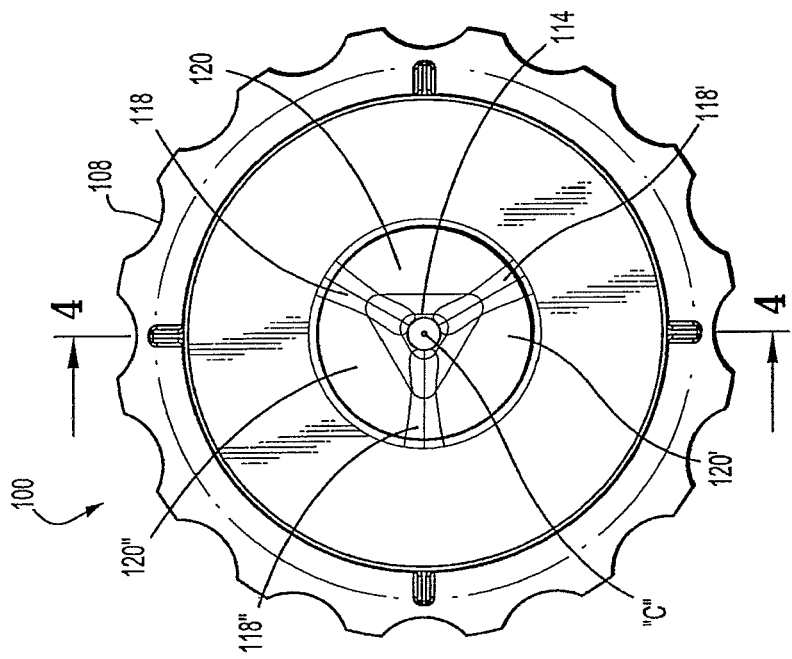
FIG. 3 is a front view of the dilating instrument of FIG. 1.

Specific embodiments of the presently disclosed apparatus will now be described in detail with reference to the foregoing figures, wherein like reference numerals identify similar or identical elements. In the figures and in the description which follows, the term "proximal", as is traditional will refer to the end of the apparatus or instrument of the present disclosure which is closest to the clinician, while the term "distal" will refer to the end of the device or instrument which is furthest from the clinician.

Referring now to the drawings, FIG. 1 illustrates a surgical portal or access apparatus 10 and a dilating surgical instrument, member, or obturator 100 in accordance with the present disclosure.

At a proximal end, access apparatus 10 includes a housing 12 configured for the internal receipt of a seal or valve, as is known in the art. Extending distally from housing 12 is a shaft or cannula 16 having respective proximal and distal ends 18, 20 and defining a lumen 22 therethrough. Housing 12, distal end 20 of cannula 16, and the lumen 22 defined therethrough are each dimensioned such that the dilating instrument 100 may pass therethrough.

Figure 2:
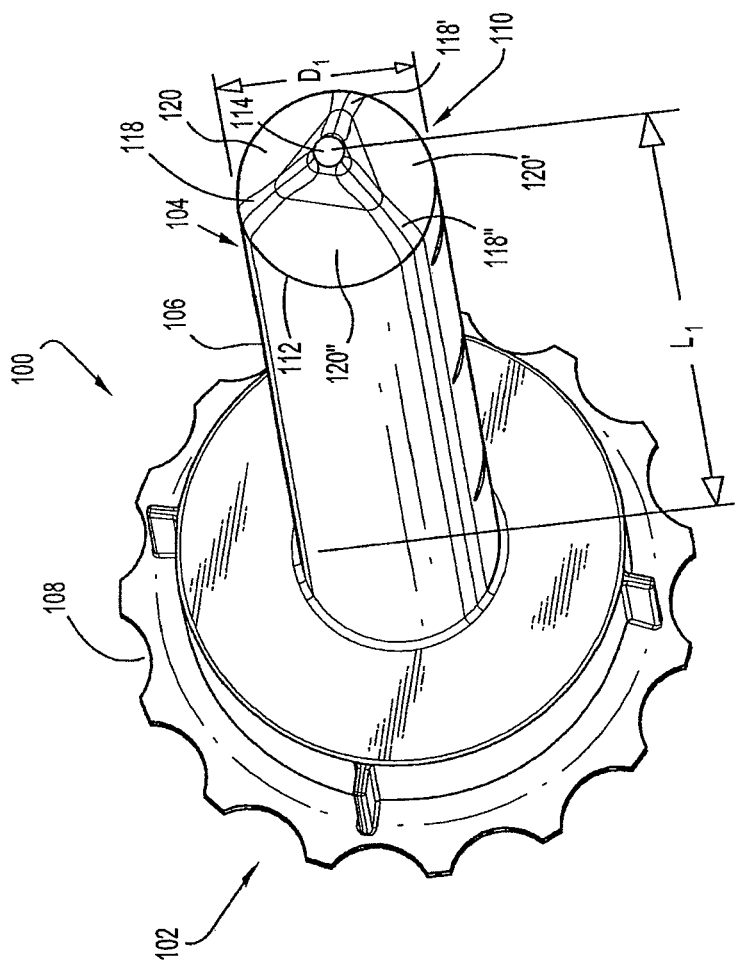
FIG. 2 is a side perspective view of the dilating instrument of FIG. 1.
Figure 11:
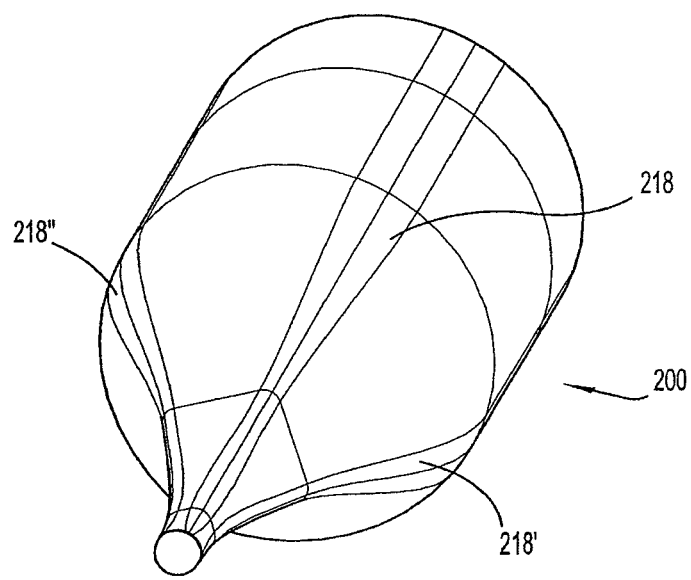
FIG. 11 is a side perspective view of an alternate embodiment of the dilating member.
Figure 12:
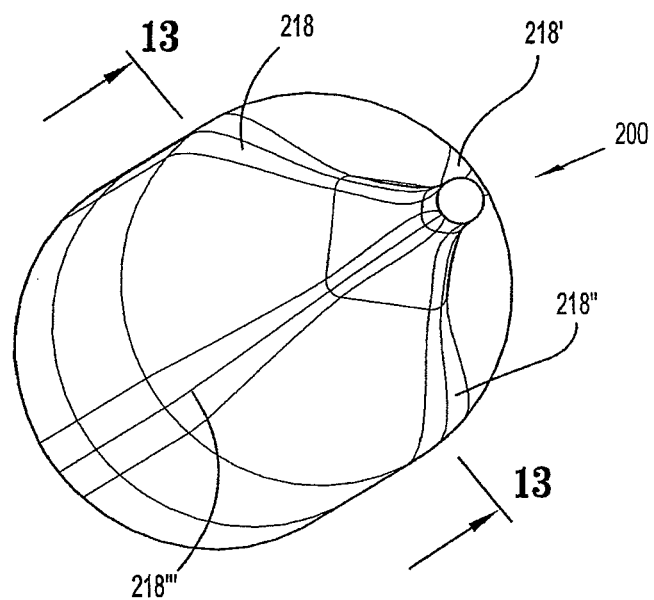
FIG. 12 is a side perspective view of the dilating member of FIG. 11.
Figure 18:
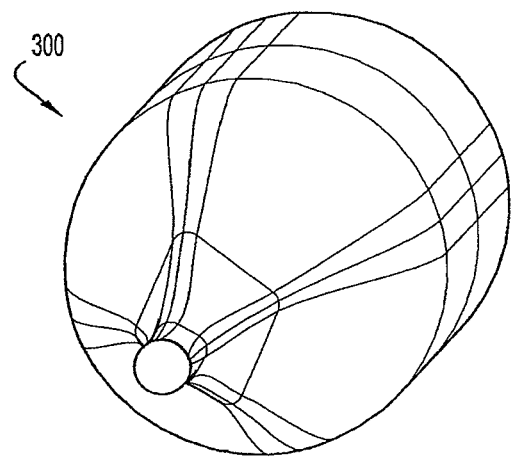
FIG. 18 is a side perspective view of another embodiment of the dilating member.
Figure 19:
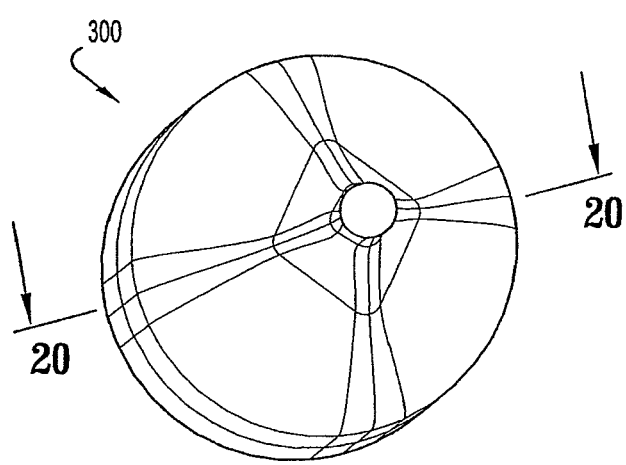
FIG. 19 is a side perspective view of the dilating member of FIG. 18.
Figure 21:
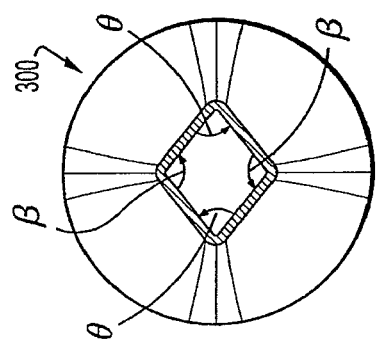
FIG. 21 is a front view of the dilating member taken along lines 21-21 of FIG. 20.
Figure 22:
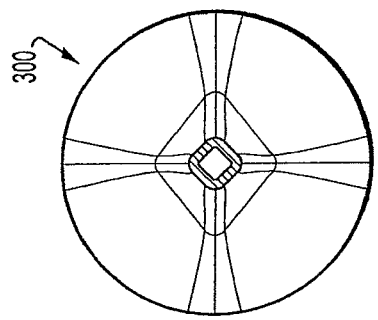
FIG. 22 is a front view of the dilating member taken along lines 22-22 of FIG. 20.

As seen in FIG. 2, dilating instrument 100 has a proximal end 102, a distal end 104, and a shaft 106 disposed therebetween. At proximal end 102, dilating instrument 100 is coupled to a gripping member 108 that is configured and dimensioned to facilitate gripping by a clinician, operator, or surgeon. In one embodiment, the gripping member may include a cushioning member or portion that is configured to at least partially absorb the force applied to the gripping member by the clinician, as well as the impact of that force upon the clinician's hand, during the distal advancement of the dilating instrument through a patient's tissue. The cushioning member may be formed of any at material that is at least semi-resilient in nature including, but not limited to, polymers.

The coupling between proximal end 102 and gripping member 108 may be either fixed or movable, e.g. pivotable, and may be either permanent or releasable.

Shaft 106 of dilating instrument 100 is an elongate member defining a diameter "$D_1$" and a length "$L_1$". Diameter "$D_1$" is of a suitable dimension such that shaft 106 does not significantly deform or buckle under the influence of the force applied to the gripping member by the clinician, as discussed above. "$D_1$" may be any diameter substantially within the range of approximately 5 mm to approximately 15 mm, as is conventional in the art. Length "$L_1$" is of any dimension suitable for the intended purpose of accessing a patient's tissue through the cannula of a surgical access apparatus. Disposed at distal end 104 of dilating instrument 100 is a dilating member 110.

Referring now to FIGS. 2-31, various embodiments of the dilating member 110 will be discussed in detail. With respect to FIGS. 2-10 in particular, dilating member 110 has a proximal end 112, a distal end or tip 114, and an outer surface 116 that extends therebetween. Dilating member 110 may be formed of any suitable biocompatible material, including but not limited to inert stainless steel, a biocompatible polymeric material or the like, and may be either a solid member or at least partially hollow.

Proximal end 112 of dilating member 110 is associated with shaft 106. In one embodiment, shaft 106 and proximal end 112 of dilating member 110 are integrally formed such that dilating member 110 and shaft 106 are fixedly connected. In this embodiment, shaft 106 and proximal end 112 of dilating member 110 may be connected in any suitable manner including, but not limited to, the use of adhesives, monolithic formation, or welding. In an alternate embodiment, shaft 106 and proximal end 112 of dilating member 110 may be releasably connected through the use of any suitable structural mechanism, including but not limited to, a screw-type or interference-fit arrangement.

Outer surface 116 of dilating member 110 includes at least one atraumatic edge member 118 that extends outwardly therefrom. Edge member or members 118 extend proximally from tip 114 to proximal end 112 of dilating member 110 along the contour of outer surface 116. In one embodiment, edge member or members 118 may extend beyond proximal end 112 of dilating member 110 and at least partially along shaft 106 of dilating instrument 100. Edge member or members 118 are substantially blunt, smooth protrusions from outer surface 116 that define at least one recessed portion 120 therebetween. Edge member or members 118 serve to lift the surrounding tissue (not shown) away from the at least one recessed portion 120 of the outer surface 116, thereby decreasing the surface area of the dilating member 110 that is in contact with the patient's tissue (not shown). By decreasing this surface area, any adhesion between the tissue (not shown) and the dilating member 110 that may otherwise occur during the insertion and distal advancement of dilating instrument 100 is substantially minimized.

In the embodiment shown in FIGS. 2-10, dilating member 110 includes three respective edge members 118-118" that define three respective recessed portions 120-120". In additional embodiments, as seen in FIGS. 11-24, dilating members 200 and 300 include four edge members 218-218''' and 318-318''', respectively. The present disclosure contemplates that dilating member 110 may include any number of edge members 118 suitable for the intended purpose of facilitating the distal advancement of the dilating instrument 100 and the dilation of a percutaneous access point.

Although edge members 118 of dilating member 110 are depicted as substantially blunt, the inclusion of one or more substantially incisive or sharp edge members, either in addition to or in place of the blunt edge members disclose above, are within the scope of the present disclosure.

In one aspect of the present disclosure, the at least one recessed portion 120 of outer surface 116 of dilating member 110 may include a plurality of indentations, scallops, or the like. These indentations further limit the surface area of the dilating member 110 that may contact the patient's tissue during use, thereby further minimizing any adhesion that may occur during the distal advancement of the dilating instrument 100 through a patient's tissue.

Figure 24:
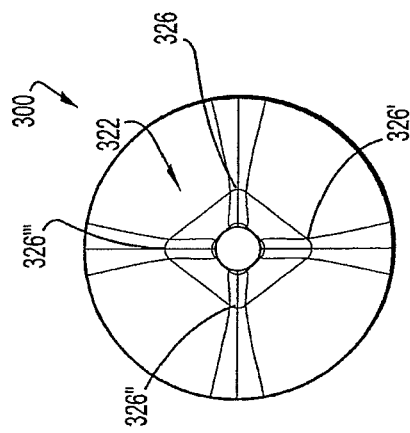
FIG. 24 is a front view of the dilating member of FIG. 18.
Figure 20:
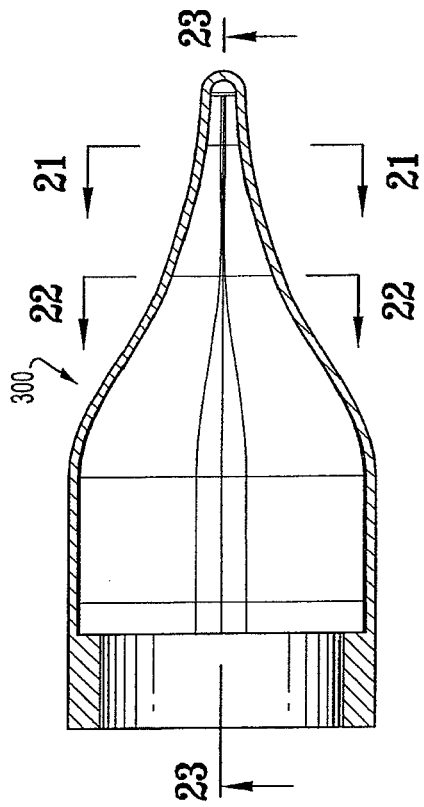
FIG. 20 is a side cross-sectional view of the dilating member of FIG. 18.
Figure 23:
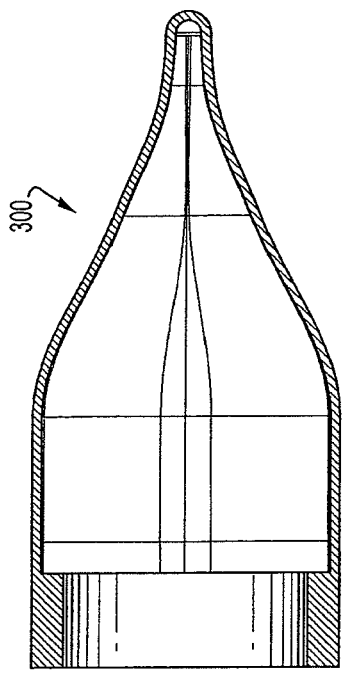
FIG. 23 is a longitudinal cross-sectional view of the dilating member taken along lines 23-23 of FIG. 20.
Figure 25:
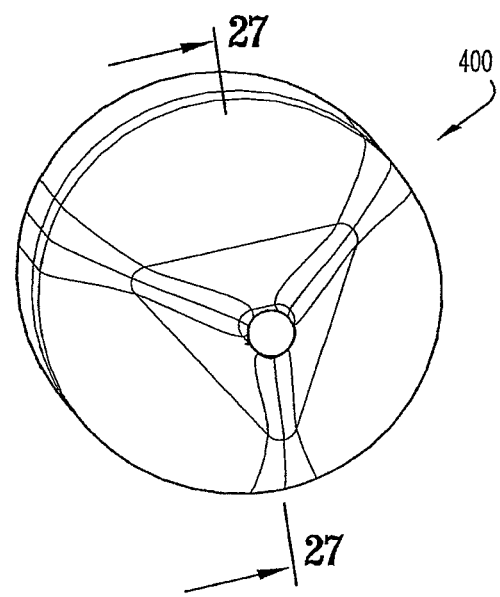
FIG. 25 is a front perspective view of another embodiment of the dilating member.
Figure 26:
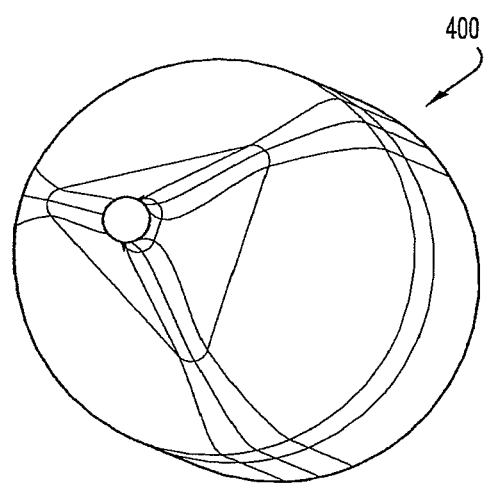
FIG. 26 is a side perspective view of the dilating member of FIG. 25.
Figure 29:
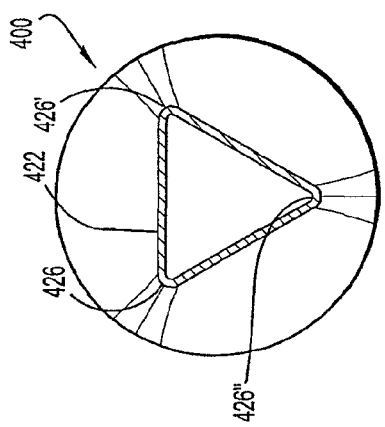
FIG. 29 is a front view of the dilating member taken along lines 29-29 of FIG. 27.
Figure 28:
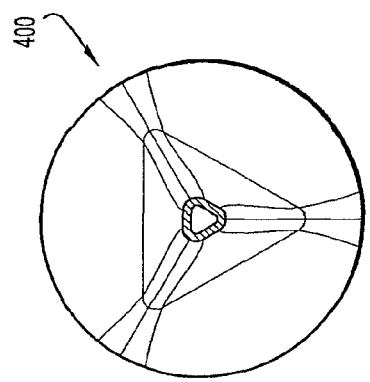
FIG. 28 is a front view of the dilating member taken along lines 28-28 of FIG. 27.
Figure 31:
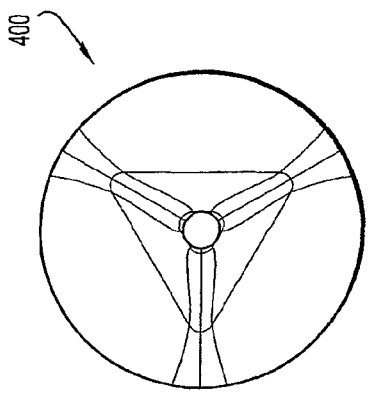
FIG. 31 is a front view of the dilating member of FIG. 25.
Figure 27:
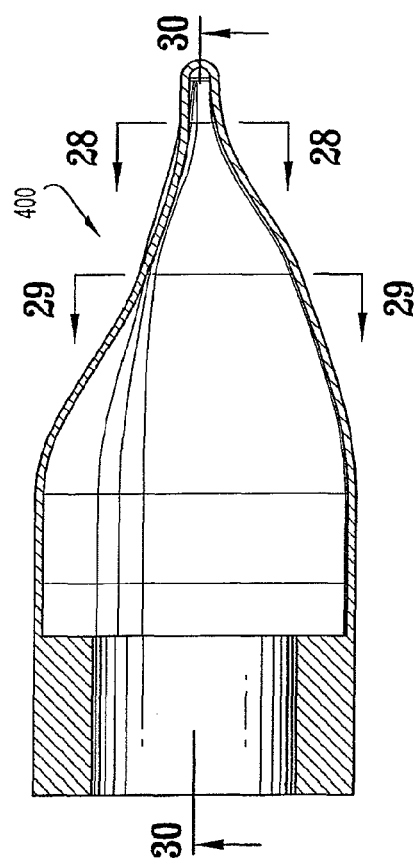
FIG. 27 is a side cross-sectional view of the dilating member of FIG. 25.
Figure 30:
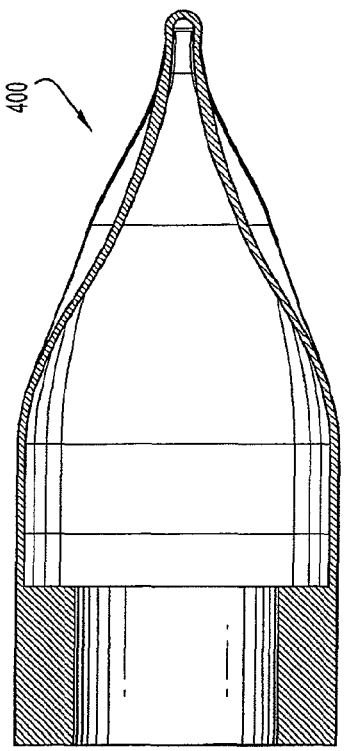
FIG. 30 is a longitudinal cross-sectional view of the dilating member taken along lines 30-30 of FIG. 27.

In one or more embodiments, the dilating member has a transverse cross-section 122 that is substantially polygonal, in that the cross-section incorporates a plurality of sides that may demonstrate a slight curvature. In the embodiment seen in FIGS. 1-8, the substantially polygonal cross-section 122 of dilating member 110 is substantially triangular, as cross-section 122 includes three sides 124-124". As seen in FIGS. 6-8, sides 124-124" of triangular cross-section 122 defines three vertices 126-126". Vertices 126-126" are substantially angular or pointed in configuration, but vertices that are substantially rounded or curved are within the scope of the present disclosure. By way of example, in one embodiment, as seen in FIGS. 24-25, dilating member 400 has a substantially triangular cross section 422 defining three vertices 426-426''' that have a substantially rounded configuration.

In the embodiment seen in FIGS. 11-17, dilating member 210 may also have a substantially polygonal cross section 222 that includes a plurality of sides 224-224''' in substantially parallel relation. In particular, dilating member 210 includes a first pair of sides 224a, which includes substantially parallel sides 224 and 224'', and a second pair of sides 224b, which includes substantially parallel sides 224' and 224'''. The points at which the first pair of sides 224a and the second pair of sides 224b intersect define four vertices 226-226'''. As seen in FIGS. 11-12 and 14-17, vertices 226-226''' are substantially rounded in configuration. However, an embodiment including four angular or pointed vertices is also within the scope of the present disclosure. Vertices 226-226''' define four angles α which are each substantially equivalent to 90° such that polygonal cross-section 222 is substantially square in configuration. In an alternate embodiment, as seen in FIGS. 18-24, vertices 326-326''' define a first pair of angles β which are less than 90° and a second pair of angles θ which are greater than 90° such that polygonal cross-section 322 resembles an elongated "diamond".

In additional embodiments, the dilating member 210 may have a substantially polygonal cross-section 222 that includes any suitable number of sides 224, including but not limited to five or six. In these additional embodiments, the substantially polygonal cross-section 222 may be substantially pentagonal, hexagonal, etc., in configuration.

Referring back to the embodiment of FIGS. 1-8, dilating member 110 defines a diameter "$D_2$" and a length "$L_2$". Diameter "$D_2$" decreases over length "$L_2$" such that dilating member 110 exhibits a substantially tapered profile "P". Diameter "D2" decreases at an intermittent or variable rate over length "L2" such that the profile "P" of dilating member 110 includes one or more concave portions 128. In an alternate embodiment, the diameter of dilating member 110 may be constantly or consistently varied over its length such that dilating member 110 may exhibit a substantially conical profile.

As discussed above, dilating member 110 includes a tip 114. Tip 114 may be substantially blunt such that dilating instrument 110 substantially minimizes any tissue trauma during the insertion and the distal advancement thereof. An embodiment that incorporates a substantially incisive tip is also within the scope of the present disclosure, however. By incorporating an incisive tip, instrument 100 would obviate the need for an initial incision or puncture in the patient's tissue with a separate implement. As seen in FIGS. 1-8, tip 114 is substantially aligned with a centerpoint "C" of dilating member 110. In an alternate embodiment, however, tip 114 may be substantially offset from centerpoint "C".

Figure 32:
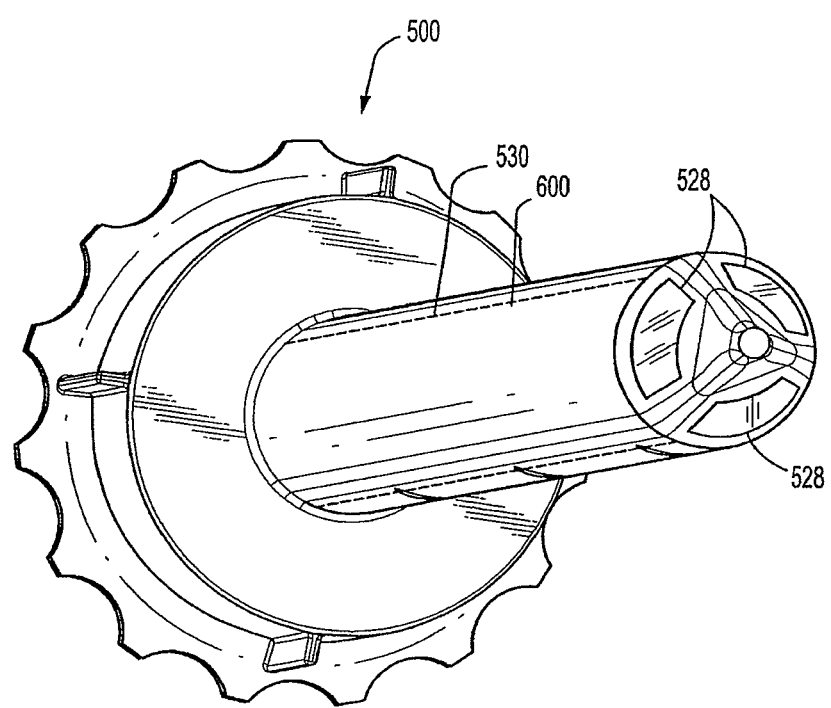
FIG. 32 is a side perspective view of another embodiment of the dilating member incorporating at least one transparent window and defining a lumen therethrough configured and dimensioned for the internal receipt of an endoscope.

Referring now to FIG. 32, dilating member 510 may include one or more transparent portions 528 such that light is permitted to pass into dilating instrument 500. Transparent portions 528 may be formed of any suitable biocompatible material that is at least translucent. In this embodiment, dilating instrument 500 defines a lumen or cavity 530 at least partially therethrough that is configured and dimensioned to receive an endoscope or other suitable viewing instrument 600 such that a clinician may view a patient's tissue (not shown) through endoscope 600 and the transparent portions 528 of dilating instrument 500 during the insertion and distal advancement thereof. Further information regarding the use of optical or transparent materials in surgical access devices may be obtained through reference to commonly assigned U.S. Pat. No. 6,685,630 to Sauer, et al., the entire contents of which are hereby incorporated by reference.

While the above is a complete description of the embodiments of the present disclosure, various alternatives, modifications and equivalents may be used. Therefore, the above description should not be construed as limiting, but rather as illustrative of the principles of the disclosure made herein. Those skilled in the art will envision other modifications within the scope and spirit of the claims appended hereto.

What is claimed is:

1. A surgical instrument for use with a surgical portal apparatus comprising:
    an elongate shaft having proximal and distal ends and defining a longitudinal axis; and
    a dilating member disposed at the distal end of the elongate shaft and including a tip, wherein an entire outer surface of the tip is atraumatic and includes:
        a first portion having a transverse cross-sectional configuration including three curvate sides curving away from the central longitudinal axis;
        a second portion extending distally from the first portion, the second portion having a transverse cross-sectional configuration including three substantially planar sides;
        a third portion extending distally from the second portion, the third portion having a transverse cross-sectional configuration including three curvate sides curving towards the central longitudinal axis.

2. The surgical instrument of claim 1, wherein the elongate shaft defines a central longitudinal axis.

3. The surgical instrument of claim 2, wherein the tip of the dilating member is aligned with the central longitudinal axis.

4. The surgical instrument of claim 2, wherein the tip of the dilating member is offset with respect to the central longitudinal axis.

5. The surgical instrument of claim 1, wherein the dilating member has a substantially tapered profile.

6. The surgical instrument of claim 1, wherein the tip of the dilating member is substantially blunt.

7. The surgical instrument of claim 1, wherein an entirety of the dilating member includes an atraumatic configuration free of any surfaces configured and dimensioned to sever tissue.

8. A surgical instrument for use with a surgical portal apparatus, comprising:
    an elongate shaft having proximal and distal ends and defining a central longitudinal axis; and
    a dilating member disposed at the distal end of the elongate shaft, the dilating member tapered distally to a curvate tip, an entirety of the dilating member being atraumatic, the dilating member including:
        a first portion having a transverse cross-sectional configuration including three sides curved away from the longitudinal axis;
        a second portion extending distally from the first portion and having a triangular transverse cross-sectional configuration including three sides; and
        a third portion extending distally from the second portion and having a transverse cross-sectional configuration including three sides, each of the first portion, the second portion, and the third portion having a different transverse cross-sectional configuration.

9. The surgical instrument of claim 8, wherein the three sides of the third portion are curved with respect to the central longitudinal axis.

10. The surgical instrument of claim 9, wherein the three sides of the third portion are curved towards the central longitudinal axis.

11. The surgical instrument of claim 8, wherein the dilating member includes an outer surface free of any surfaces configured and dimensioned to sever tissue.

12. A surgical instrument for use with a surgical portal apparatus, comprising:
- an elongate shaft having proximal and distal ends and defining a central longitudinal axis; and
- an atraumatic dilating member disposed at the distal end of the elongate shaft, the dilating member tapered distally to a curvate tip, the dilating member including:
  - a first portion having a transverse cross-sectional configuration including three curvate sides curved away from the longitudinal axis;
  - a second portion extending distally from the first portion and having a transverse cross-sectional configuration including three planar sides, each planar side being joined to an adjacent planar side by a convex connecting segment; and
  - a third portion extending distally from the third portion and having a transverse cross-sectional configuration including three curvate sides.

13. The surgical instrument of claim 12, wherein the three sides of the third portion are curved with respect to the central longitudinal axis.

14. The surgical instrument of claim 13, wherein the three sides of the third portion are curved towards the central longitudinal axis.

15. The surgical instrument of claim 12, wherein an entirety of the dilating member includes an outer surface free of any surfaces configured and dimensioned to sever tissue.

* * * * *